United States Patent [19]

Mishra et al.

[11] Patent Number: 5,684,142

[45] Date of Patent: Nov. 4, 1997

[54] MODIFIED NUCLEOTIDES FOR NUCLEIC ACID LABELING

[75] Inventors: Nrusingha C. Mishra, Germantown, Md.; Hossein S. Khorshidi, Vienna, Va.; Yuxiang Gan, Bethesda, Md.; Pam Szweda, Cleveland Heights, Ohio; Jay George, Gaithersburg, Md.

[73] Assignee: Oncor, Inc., Gaithersburg, Md.

[21] Appl. No.: 485,147

[22] Filed: Jun. 7, 1995

[51] Int. Cl.$^6$ .................. C07H 19/00; C07H 21/02; C12Q 1/68

[52] U.S. Cl. ............... 536/22.1; 435/6; 536/23.1; 536/27.1

[58] Field of Search ................ 435/6; 536/22.1, 536/23.1, 27.1

[56] References Cited

U.S. PATENT DOCUMENTS

| | | | |
|---|---|---|---|
| 4,711,955 | 12/1987 | Ward et al. | 536/29 |
| 4,828,979 | 5/1989 | Klevan et al. | 435/6 |
| 4,895,955 | 1/1990 | Ford et al. | 548/303 |
| 4,948,882 | 8/1990 | Ruth | 536/27 |
| 5,013,831 | 5/1991 | Stavrianopoulos | 536/27 |
| 5,241,060 | 8/1993 | Engelhardt et al. | 536/27 |
| 5,405,950 | 4/1995 | Mock et al. | 536/25.32 |
| 5,407,801 | 4/1995 | Miller | 435/6 |

OTHER PUBLICATIONS

Bergstrom et al. "Organoiron-mediated alkylation of phosphite esters: Synthesis of (dicarbonyl)(n$^5$-cyclopentadienyl)iron-derived nucleoside phosphonate esters" J. Org. Chem., vol. 57, pp. 873–876 1992.

Neidlein et al. "Syntheses and investigations of [Oxazolo 2,3-a isoindol-9b(2H)-yl]phosphonates and -phosphinates: a new class of heterocycles" Helevetica Chimica Acta, vol. 76, pp. 2407–2417 1993.

Jois et al., "Synthesis and antiviral evaluation of some novel [1,2,4]triazolo[4,3-b][1,2,4]triazole nucleoside analogs" J. Hetercyclic Chem. vol. 30, p. 1289 1993.

"Enzymatic synthesis of biotin–labeled polynucleotides: Novel nucleic acid affinity probes", Pennina R. Langer et al, Proc. Natl. Acad. Sci. USA, vol. 78, No. 11, pp. 6633–6637, Nov. 1981, Biochemistry.

"Immunological method for mapping genes on *Drosophila* polytene chromosomes", Pennina R. Langer-Safer et al, Proc. Natl. Acad. Sci. USA, vol. 79, pp. 4381–4385, Jul. 1982, Genetics.

"Attachment of Protein affinity–labeling reagents of variable length and amino acid specificity to E. coli TRNA$^{fMet}$," LaDonne H. Schulman et al, Nucleic Acids Research, vol. 9, No. 5, pp. 1203–1217, Mar. 11, 1981.

"A Method for Linking Fluorescent Labels to Polynucleotides: Application to Studies of Ribosome–Ribonucleic Acid Interactions", David E. Draper et al, Biochemistry, 19, pp. 1774–1781, 1980.

"Chemistry of Nucleosides and Nucleotides", Leroy B. Townsend, vol. 1, pp. 8–41 1988.

"Synthesis of DNA Containing Modified Bases by Postsynthetic Substitution. Synthesis of Oligomers Containing 4–Substituted Thymine: O$^4$–Alkylthymine, 5–Methylcytosine, N$^4$–(Dimethylamino)–5–methylcytosine, and 4–Thiothymine", Yao–Zhong Xu et al, J. Org. Chem, 57, pp. 3839–3845, 1992.

"Facile Addition of Hydroxylic Nucleophiles to the Formyl Group of Uridine–6–carboxaldehydes", Michael P. Groziak et al, The Journal of Organic Chemistry, vol. 57, pp. 940–944, 1992.

"A facile and regiospecific preparation of 6–alkyluridines", Hiromichi Tanaka et al, Nucleic Acids Research, Symposium Series No. 8, pp. s33–s36 1980.

"Synthesis of isotope labeled oligonucleotides and theiruse in an NMR study of a protein–DNA complex", E.R. Kellenbach et al, Nucleic Acids Research, vol. 20, No. 4, pp. 653–657, (1992).

"Regiospecific C–Alkylation of Uridine: A simple Route to 6–Alkyluridines", Hiromichi Tanaka et al, Tetrahedron Letters No. 19, pp. 4755–4758, 1979.

"Formation of 5–and 6–Aminocytosine Nucleosides and Nucleotides from the Corresponding 5–Bromocytosine Derivatives: Synthesis and Reaction Mechanism", David Goldman et al, Nucleosides & Nucleotides, 2(2), pp. 175–187, 1983.

"A Novel Cyclization Reaction of A C–6 Substituted Uridine Analog: An Entry to 5,6–Dialkylated Uridine Derivatives", Binghe Wang et al, Tetrahedron letters, vol. 30, No. 50, pp. 7005–7008, 1989.

"Conformational Properties of a Novel Modified Nucleoside, 5–Formycytidine, Found at the First Position of the Anicodon of Bovine Mitochondrial tRNA$^{Meth}$", Gota Kawai et al, Nucleosides and Nucleotides, 13(5), pp. 1189–1199, 1994.

"Oligonucleotides Derived from 5–(1–Propynyl)–2'–O–Allyl–Uridine and 5–(1–Propynyl)–2'–O–Allyl–Cytidine: Synthesis and RNA Duplex Formation", Brian C. Froehler et al, Tetrahedron Letters, vol. 34, No. 6, pp. 1003–1006, 1993.

"Oligodeoxynucleotides Containing C–5 Propyne analogs of 2'–Deoxyuridine and 2'–Deoxycytidine", Brian C. Froehler et al, Tetrahedron Letters, vol. 33, No. 37, pp. 5307–5310, 1992.

"Antisense Gene Inhibition by Oligonucleotides Containing C–5 Propyne Pyrimidines", Richard W. Wagner et al, Science, vol. 260, pp. 1510–1513, Jun. 4, 1993.

"A Convenient Method for the Direct Incorporation of 5–Fluoro–2'–deoxycytidine into Oligodeoxynucleotides", Canio J. Marasco, Jr. et al, J. Org. Chem, 57, pp. 6363–6365.

"Antisense oligodeoxynucleotides: synthesis, biophysical and biological evaluation of oligodeoxynucleotides containing modified pyrimidines", Yogesh S. Sanghvi et al, Nucleic Acids Research, vol. 21, No. 14, pp. 3197–3203, 1993.

"Synthesis of Fluorescent or Biotinylated Nucleoside Compounds", S.R. Sarfati et al, Tetrahedron, vol. 43, No. 15, pp.3491–3497, 1987.

"Chemical Conversion of Thymidine into 5–Methyl–2'–deoxycytidine", Wing L. Sung, J.C.S.Chem. Comm., p. 1089, 1981.

*Primary Examiner*—Ardin H. Marschel
*Assistant Examiner*—Jezia Riley
*Attorney, Agent, or Firm*—Glenn E. Karta

[57] ABSTRACT

Modified pyrimidine bases and nucleotides containing a linker arm and a detectable reporter group for nucleic acid labeling. The modified nucleotides have the structure:

-$R_1$ is —H or —OH;

-$R_2$ and -$R_3$ are independently —H, —OH, monophosphate, diphosphate, triphosphate, thio analogs of mono-, di-, or triphosphates, —O— attached to a reactive phosphorous-containing group or —O— protected by a blocking group;

-A and -B are independently —H, an electron donating group, an electron withdrawing group, $C_1$–$C_4$ alkyl, halogen, nitro, —COOH, amino, substituted amino, cyano, —CONH, —CSNH, —COO$R_4$ $$-\overset{O}{\underset{O}{\overset{\|}{\underset{\|}{S}}}}-, \quad -\overset{O}{\underset{O}{\overset{\|}{\underset{\|}{S}}}}R_4,$$

—CSO$R_4$, —COS$R_4$, —S$R_4$, —CO$R_4$, —CH$_2$NHR$_4$, -$R_4$C=CR$_5$H or —C≡C—$R_4$ where $R_4$ and $R_5$ are independently H, an electron donating group, an electron withdrawing group, $C_1$–$C_4$ alkyl, halogen, nitro, COOH, amino, substituted amino, cyano, CONH or CSNH;

-X- is —NH—, —NHNH—, —O—, —S—, $$-\overset{O}{\underset{O}{\overset{\|}{\underset{\|}{S}}}}-$$

or —CH$_2$—;

Rep is a detectable reporter group; and

-L- is —(CH$_2$)$_n$-(T)$_q$—(CH$_2$)$_m$Z$_1$ or —(CH$_2$)$_n$-(T)$_q$—(CH$_2$)$_m$-Z$_2$—(CH$_2$)$_p$Z$_1$ where n, m and p are each independently an integer from 1 to 20 and q is 1 or 2, -T- is —O—, —S—, $$-\overset{O}{\underset{O}{\overset{\|}{\underset{\|}{S}}}}-,\ -\overset{O}{\underset{\|}{\overset{\|}{P}}}-,\ -O-\overset{O}{\underset{\|}{\overset{\|}{P}}}-O-,\ -O-\overset{O}{\underset{O_-}{\overset{\|}{P}}}-,\ -O-\overset{O}{\underset{O_-}{\overset{\|}{P}}}-O-,$$

—NH— or a heterocyclic structure containing one or more Group Va or VIa elements as a ring atom, $Z_1$ is a covalent bond, —NH—, —CO—, —O—, —S— or $$-\overset{O}{\underset{O}{\overset{\|}{\underset{\|}{S}}}}-,$$

and -$Z_2$— is —NH—, —NHCO—, —NHCS—, —CONH—, —CSNH—, —O—, —S— or $$-\overset{O}{\underset{O}{\overset{\|}{\underset{\|}{S}}}}-.$$

21 Claims, 11 Drawing Sheets

MODIFIED NUCLEOTIDES FOR NUCLEIC ACID LABELING

BACKGROUND OF THE INVENTION

1. Field of the Invention

The present invention relates to improved modified pyrimidine bases and nucleotides containing a linker arm and a detectable reporter group for nucleic acid labeling.

2. Description of the Related Art

Modified nucleotides carrying a detectable moiety (i.e., reporter), either radioisotopic or non-radioisotopic, are useful in nucleic acid probes and oligonucleotide labeling. One common type of nucleic acid probe contains at least one modified nucleotide that has a reporter group attached via a linker arm to the base. For example, Langer et al (Proc. Natl. Acad. Sci. U.S.A., 78(11):6633–6637, 1981) describes the attachment of biotin to the C-5 position of dUTP by an allylamine linker arm. The attachment of biotin and other reporter groups to the 5-position of pyrimidines via a linker arm is also discussed in U.S. Pat. No. 4,711,955. Nucleotides labeled via a linker arm attached to the 5- or other positions of pyrimidines are also suggested in U.S. Pat. No. 4,948,882.

Bisulfite-catalyzed transamination of the $N^4$-position of cytosine with bifunctional amines is described by Schulman et al (Nucleic Acids Research, 9(5): 1203–1217, 1981) and Draper et al (Biochemistry, 19: 1774–1781, 1980). By this method, fluorescent labels are attached via linker arms to cytidine or cytidine-containing polynucleotides. The attachment of biotin to the $N^4$-position of cytidine is disclosed in U.S. Pat. No. 4,828,979, and the linking of detectable moieties to cytidine at the $N^4$-position is also set forth in U.S. Pat. Nos. 5,013,831 and 5,241,060.

U.S. Pat. No. 5,407,801 describes the preparation of an oligonucleotide triplex wherein a linker arm is conjugated to deoxycytidine via bisulfite-catalyzed transamination. The linker arms include an aminoalkyl or carboxyalkyl linker arm.

U.S. Pat. No. 5,405,950 describes cytidine analogs in which a linker arm is attached to the $N^4$-position of the cytosine base. The linker arm is terminated with a protecting group which prevents the penultimate residue of the linker arm from reacting with the N-hydroxysuccinimide ester of biotin amino caproic acid.

While the art has made significant strides in the past, there is a need for modified nucleotides which have the ability to replace one or more natural nucleotides in single or double stranded DNA or RNA for use in gene and nucleic acid labeling.

OBJECTS AND SUMMARY OF THE INVENTION

It is therefore a general object of the present invention to provide an improved modified nucleotide for gene and nucleic acid labeling.

It is a more specific object of the present invention to provide a pyrimidine base analog or a pyrimidine nucleotide analog in which a reporter group is attached via a linker arm to the 4-position of a pyrimidine base.

It is another object of the present invention to provide a pyrimidine base analog or pyrimidine nucleotide analog to which a reporter group is attached via a linker arm having the structure —$(CH_2)_n$-$(T)_q$—$(CH_2)_m Z_1$ or —$(CH_2)_n$-$(T)_q$—$(CH_2)_m$-$Z_2$—$(CH_2)_p Z_1$ where n, m and p are each independently an integer from 1 to 20 and q is 1 or 2, -T- is

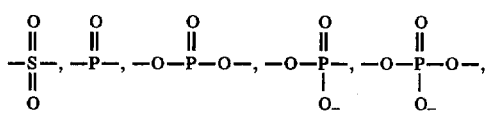

—NH— or a heterocyclic structure containing one or more Group Va or VIa elements as a ring atom, $Z_1$ is a covalent bond, —NH—, —CO—, —O—, —S— or

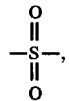

and -$Z_2$- is —NH—, —NHCO—, —NHCS—, —CONH—, —CSNH—, —O—, —S— or

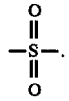

Accordingly, in one aspect the present invention provides a compound having the structure:

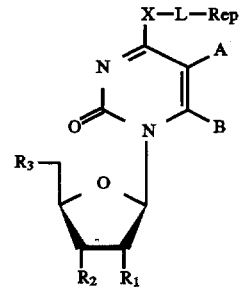

wherein:

-$R_1$ is —H or —OH;

-$R_2$ and -$R_3$ are independently —H, —OH, monophosphate, diphosphate, triphosphate, thio analogs of mono-, di-, or triphosphate, —O— attached to a reactive phosphorous-containing group or —O— protected by a blocking group;

-A and -B are independently —H, an electron donating group, an electron withdrawing group, $C_1$–$C_4$ alkyl, halogen, nitro, —COOH, amino, substituted amino, cyano, —CONH, —CSNH, —$COOR_4$,

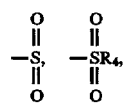

—$CSOR_4$, —$COSR_4$, —$SR_4$, —$COR_4$, —$CH_2NHR_4$, -$R_4C$=$CR_5H$ or —C≡C—$R_4$ where $R_4$ and $R_5$ are independently H, an electron donating group, an electron withdrawing group, $C_1$–$C_4$ alkyl, halogen, nitro, COOH, amino, substituted amino, cyano, CONH or CSNH;

-X- is —NH—, —NHNH— —O—, —S—,

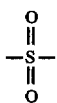

or —CH$_2$—;
Rep is a detectable reporter group; and
-L- is —(CH$_2$)$_n$-(T)$_q$—(CH$_2$)$_m$Z$_1$ or —(CH$_2$)$_n$-(T)$_q$—(CH$_2$)$_m$-Z$_2$—(CH$_2$)$_p$Z$_1$ where n, m and p are each independently an integer from 1 to 20 and q is 1 or 2, -T- is —O—, —S—,

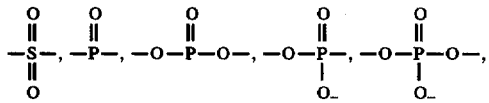

—NH— or a heterocyclic structure containing one or more Group Va or VIa elements as a ring atom, Z$_1$ is a covalent bond, —NH—, —CO—, —O—, —S— or

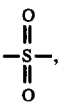

and -Z$_2$- is —NH—, —NHCO—, —NHCS—, —CONH—, —CSNH—, —O—, —S— or

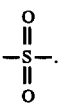

In another aspect the present invention provides a compound having the structure:

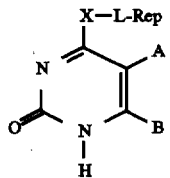

wherein -A, -B, -X-, -L- and Rep are as described above.

BRIEF DESCRIPTION OF THE DRAWINGS

FIG. Ia illustrates an analytical HPLC chromatogram for OBEA-dCTP [II].

FIG. Ib illustrates an HPLC chromatogram for the purification of OBEA-dCTP [II].

Figure 1A:
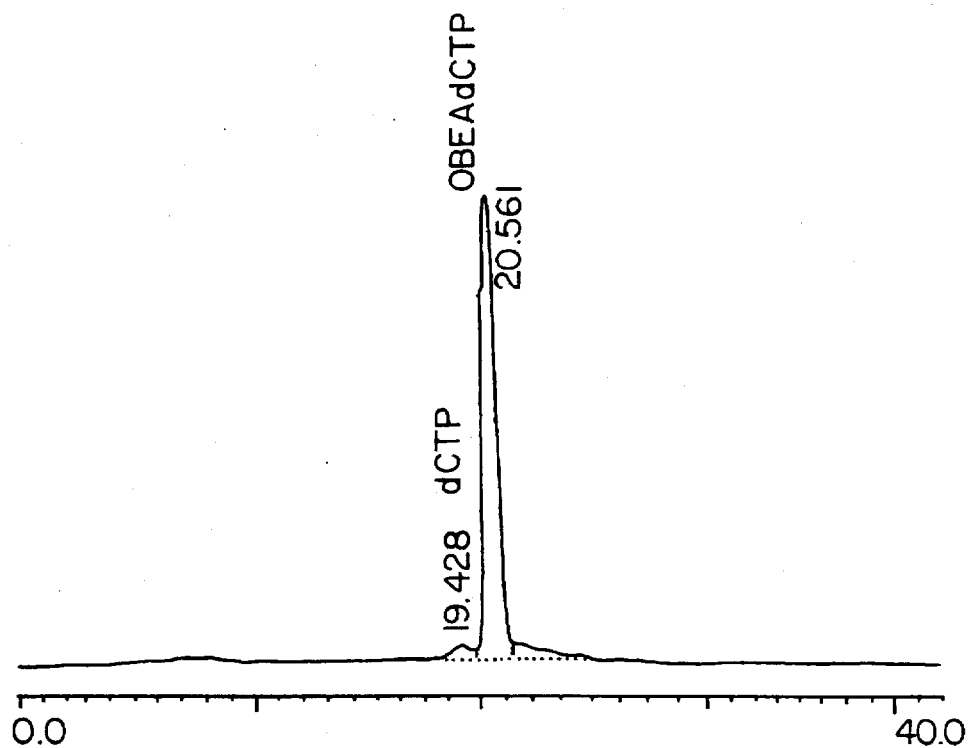
Figure 1B:
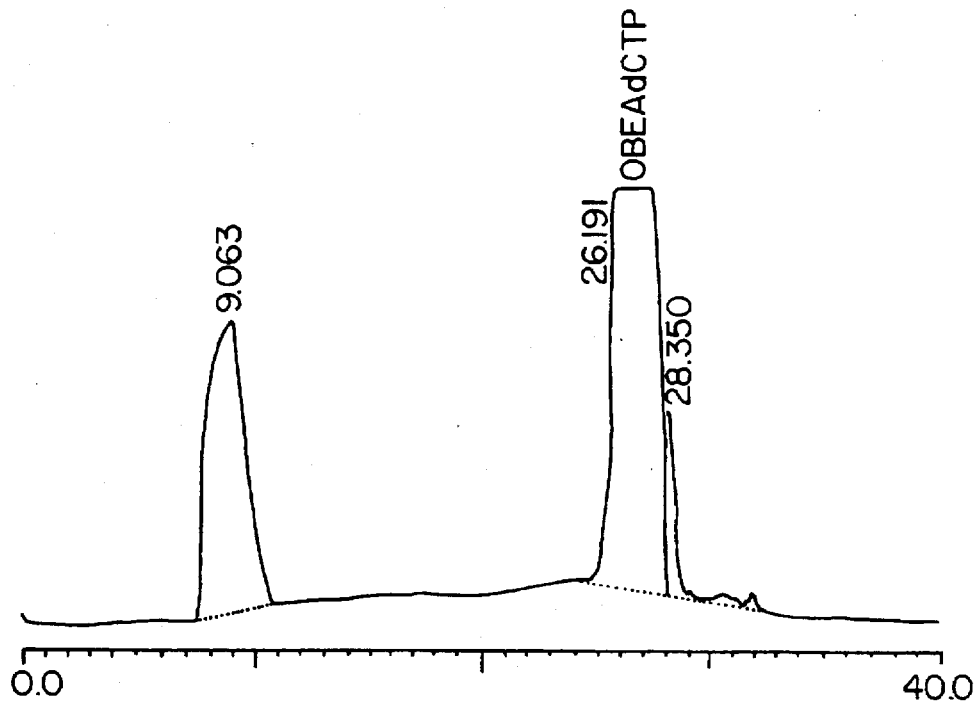
Figure 2A:
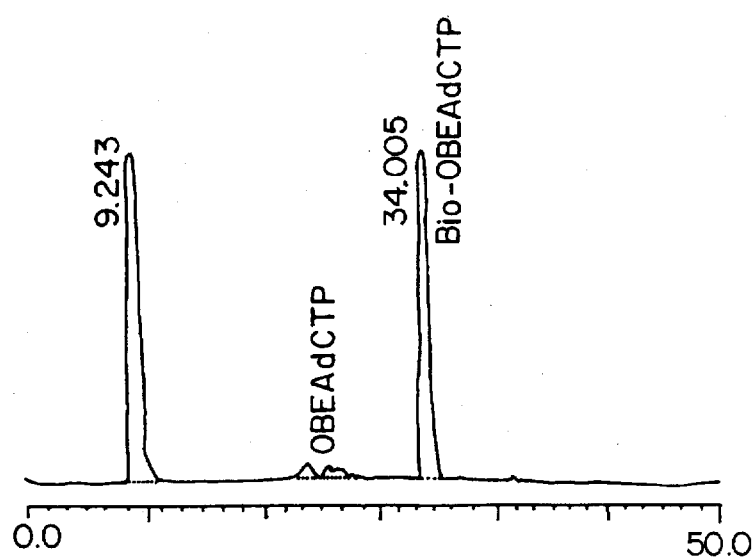
Figure 2B:
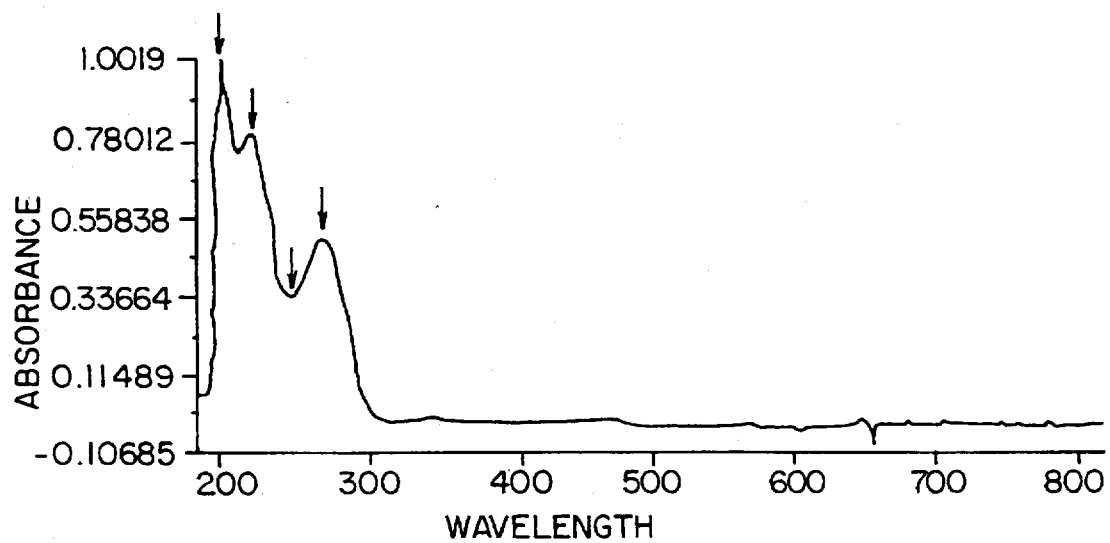
Figure 2C:
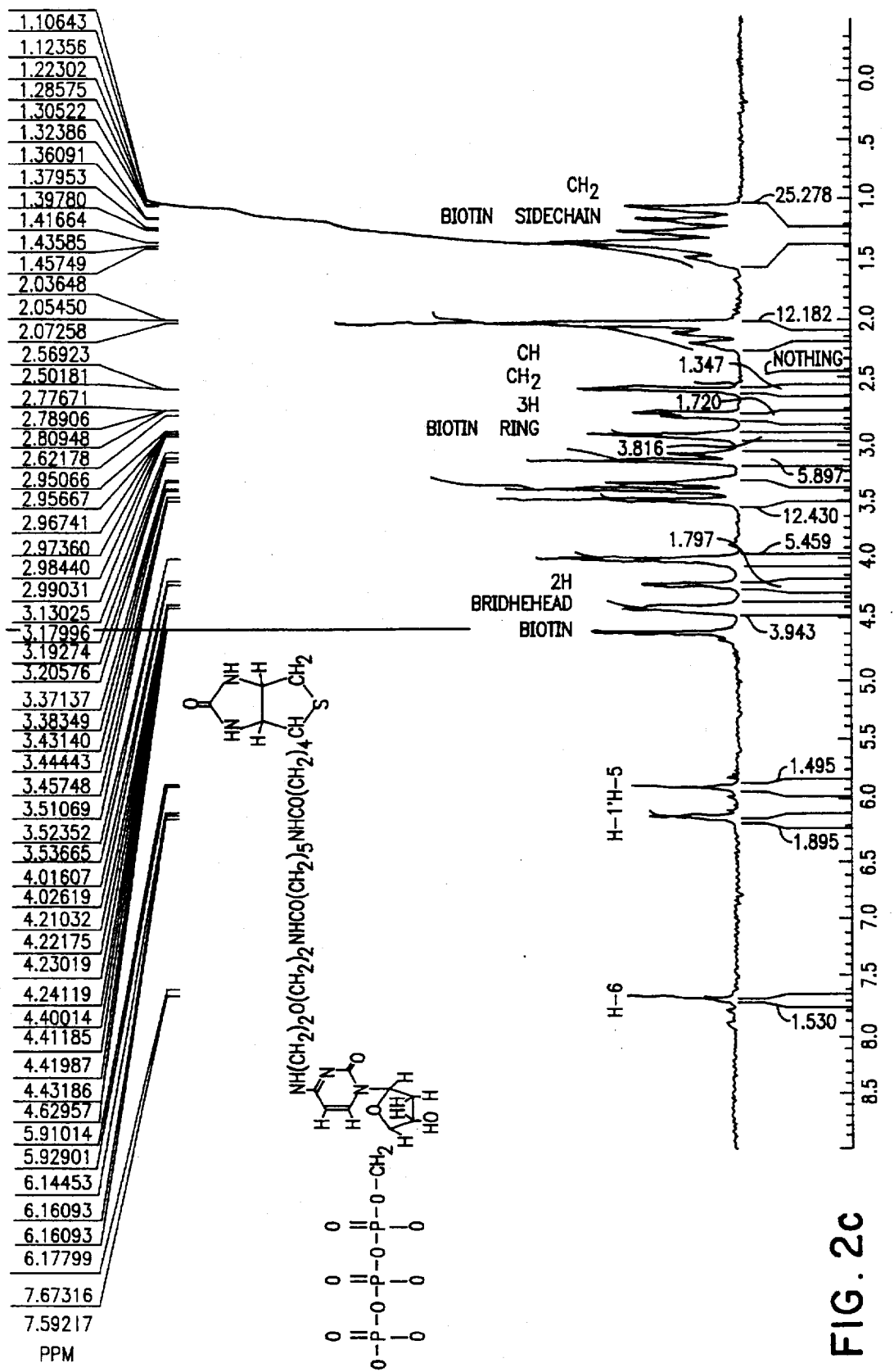
Figure 3A:
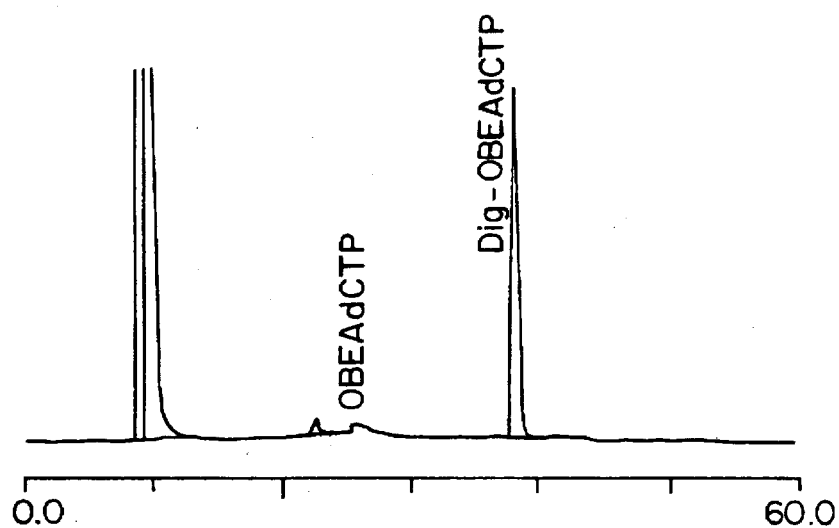
Figure 3B:
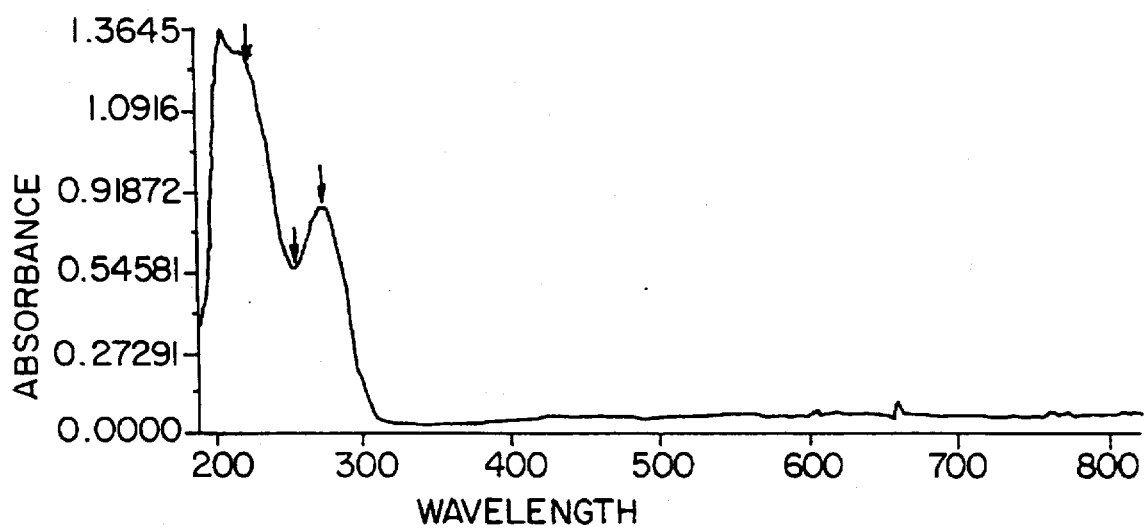
Figure 3C:
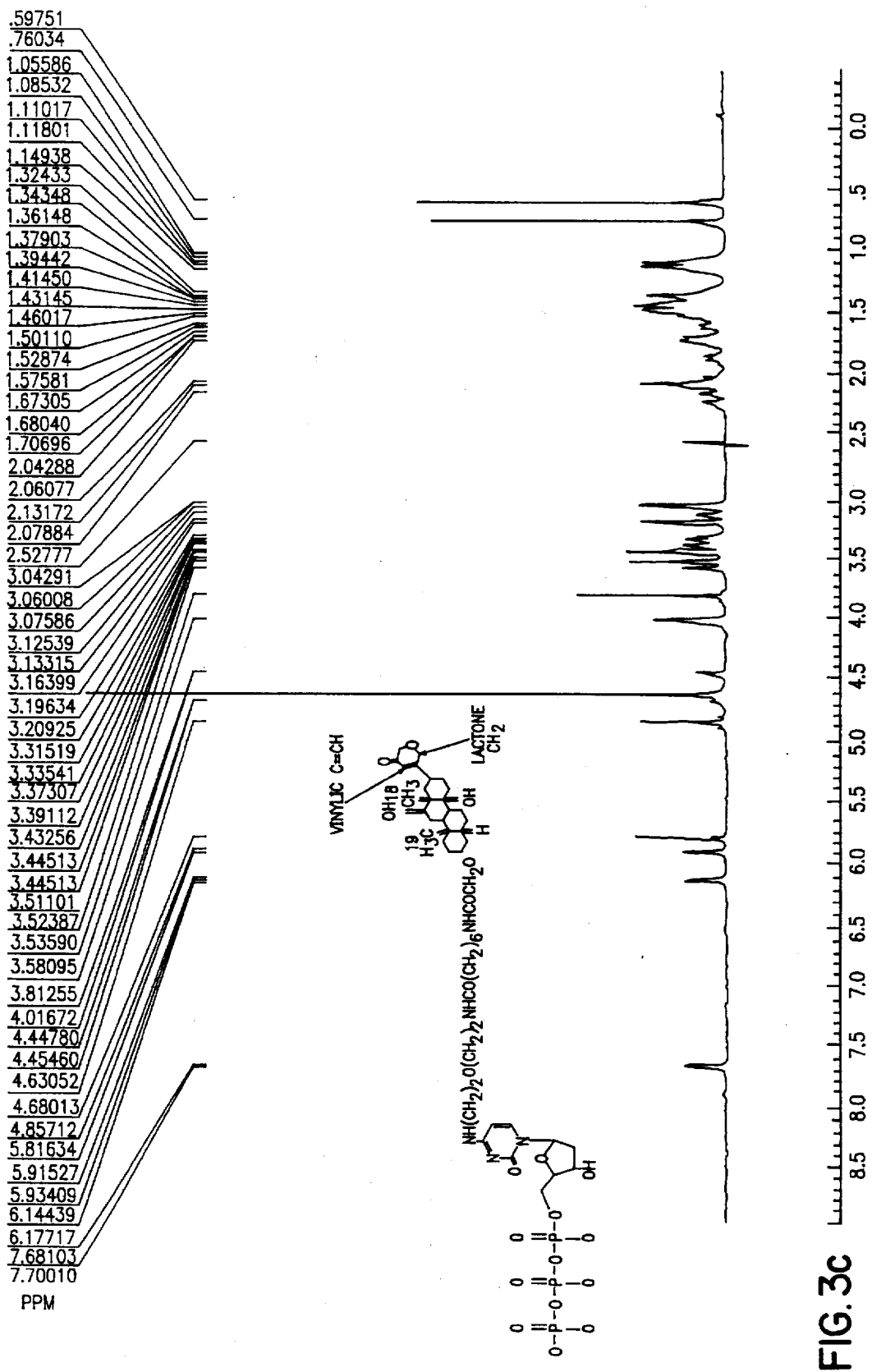
Figure 4A:
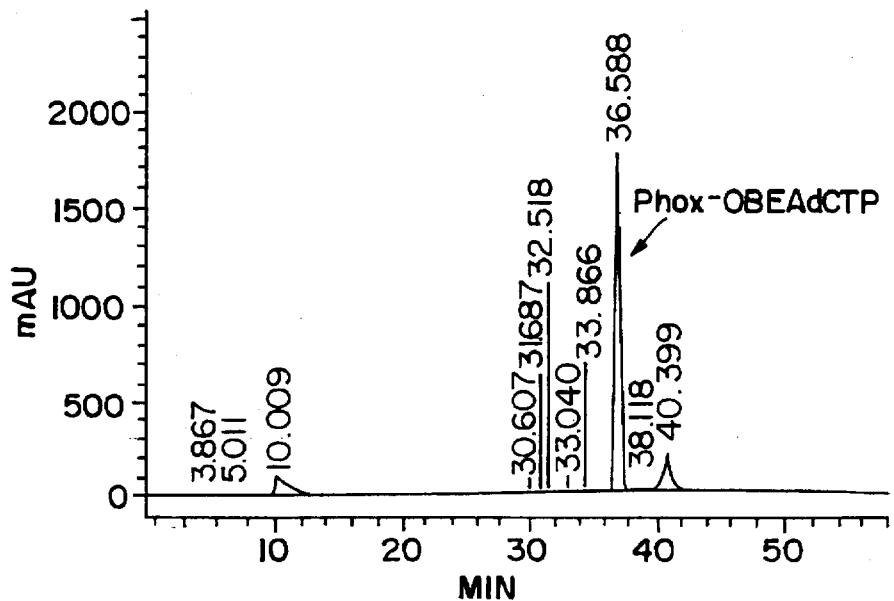
Figure 4B:
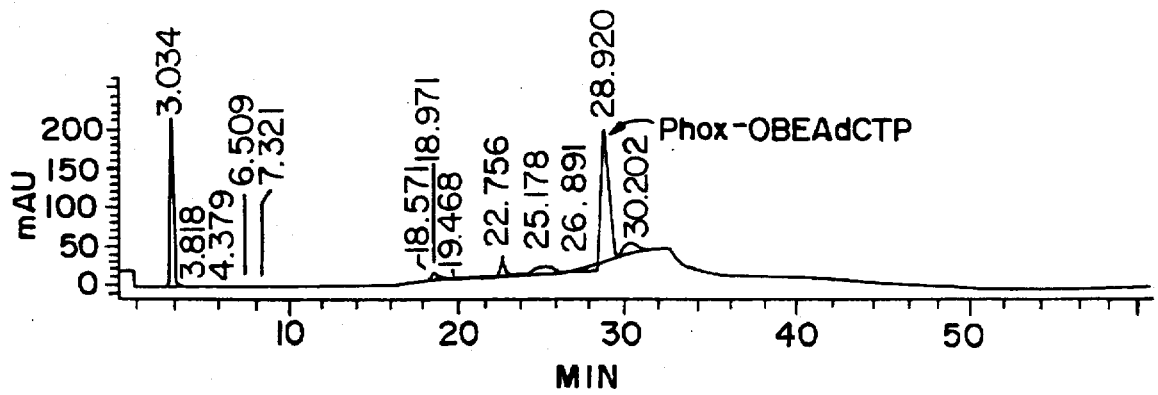
Figure 4C:
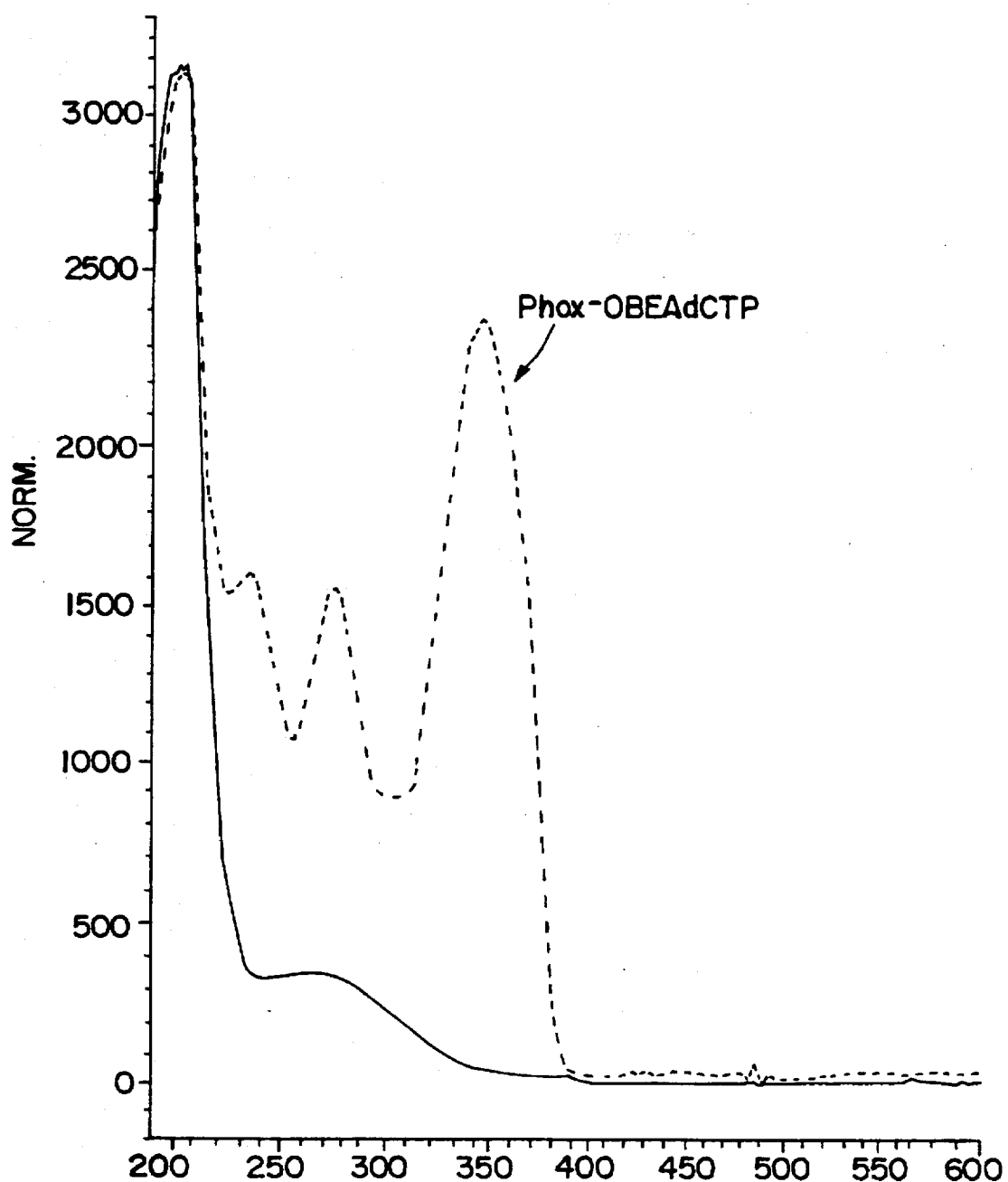
Figure 5A:
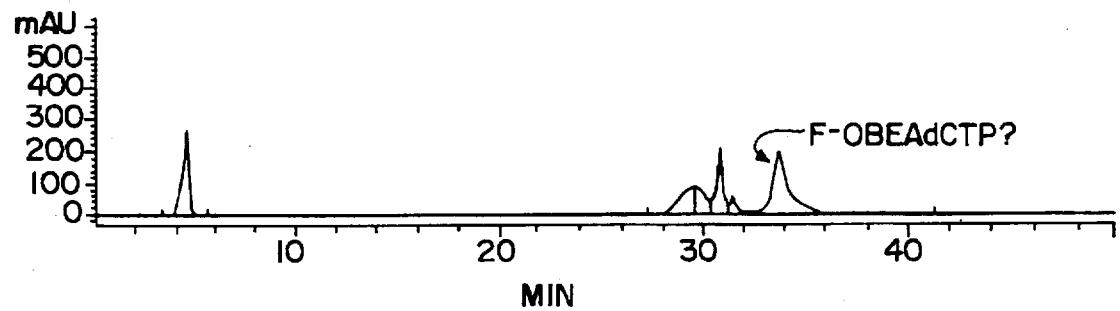
Figure 5B:
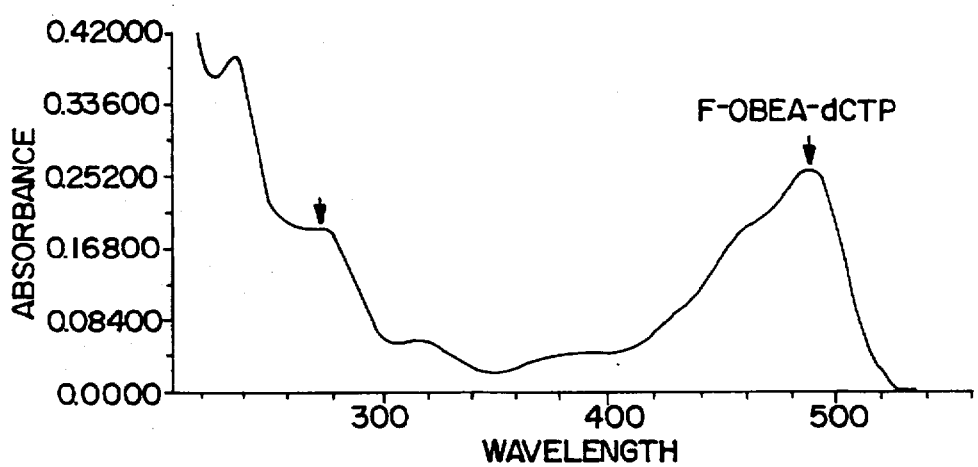
Figure 6A:
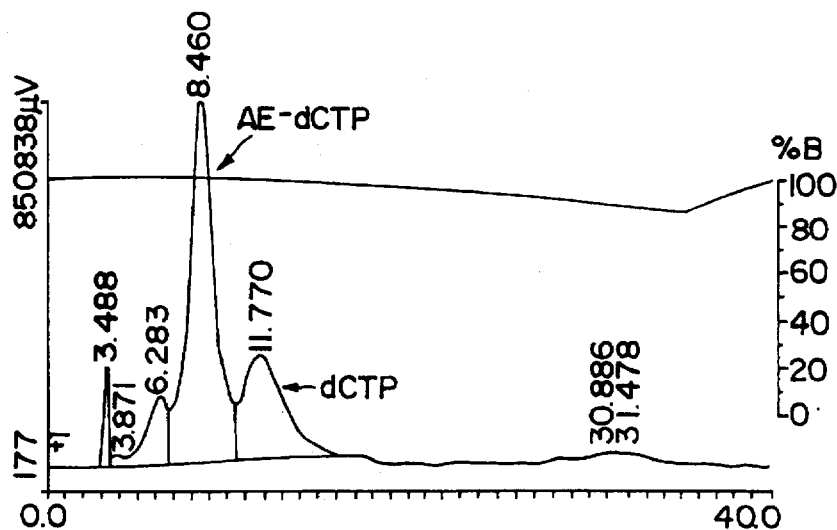
Figure 6B:
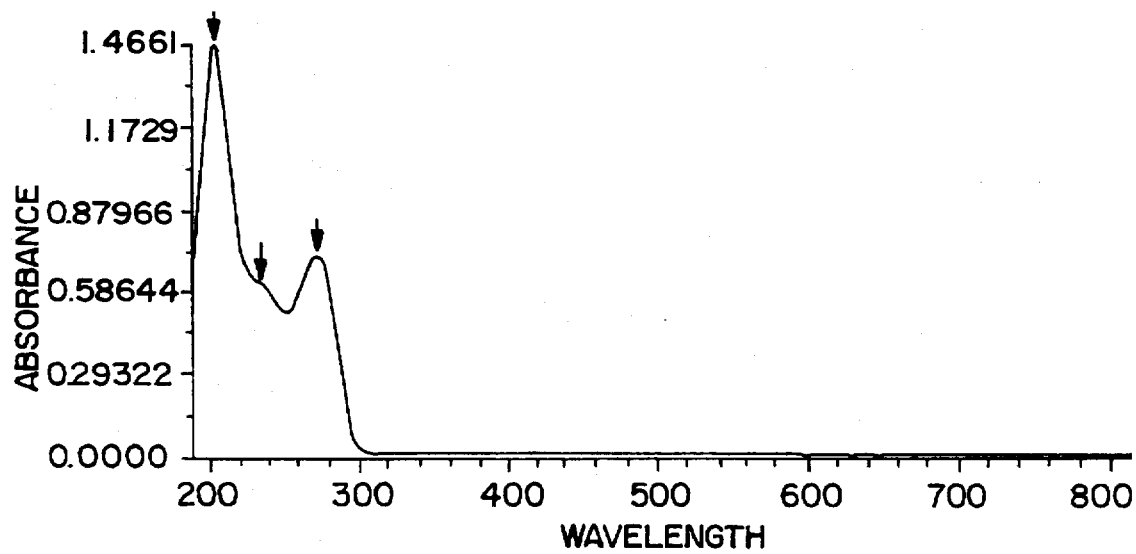
Figure 7A:
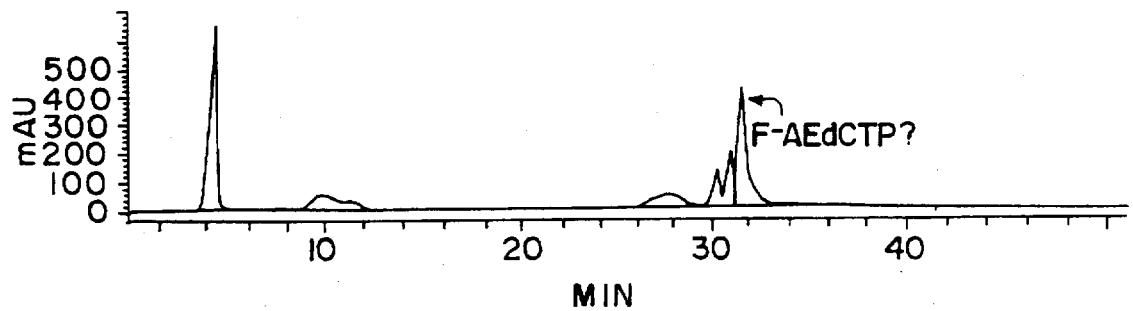
Figure 7B:
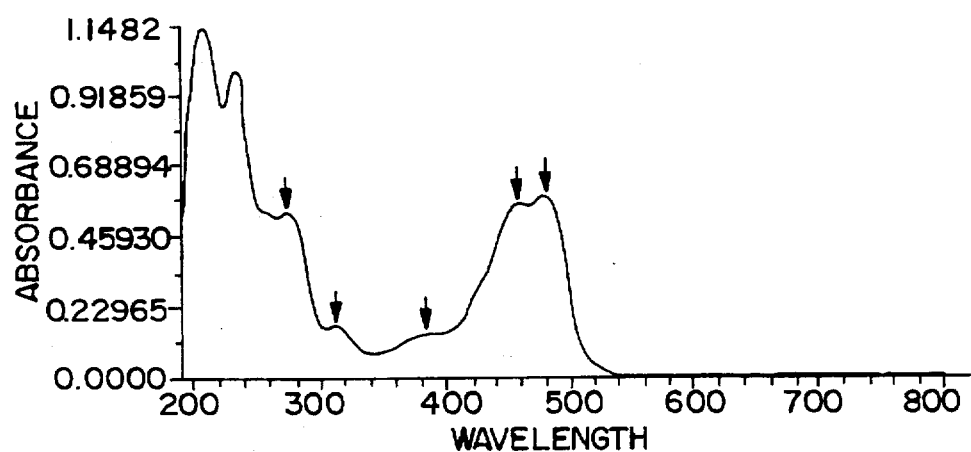
Figure 8A:
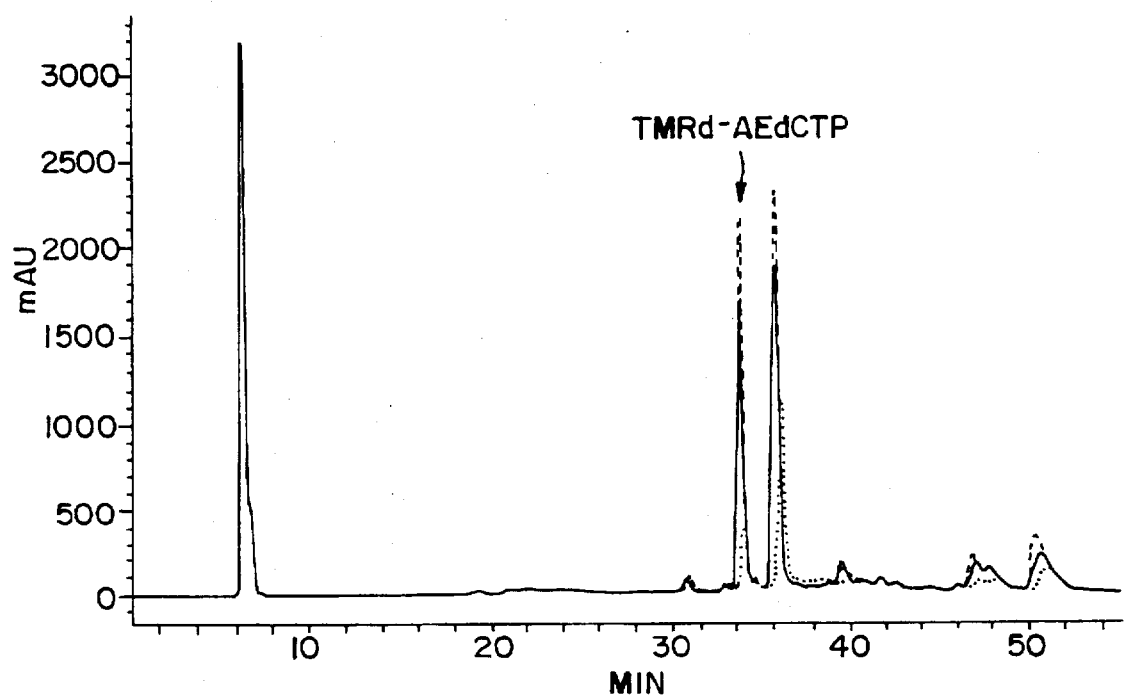
Figure 8B:
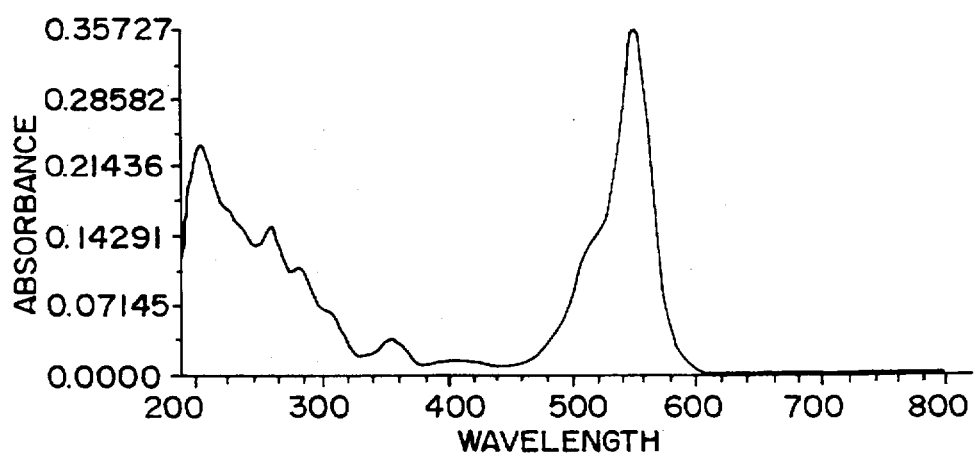

FIG. IIa illustrates an HPLC chromatogram for the purification of Bio-OBEAdCTP [III].

FIG. IIb illustrates the UV spectrum of Bio—OBEAdCTP [III].

FIG. IIc illustrates the $^1$H-NMR spectrum of Bio—OBEAdCTP [III].

FIG. IIIa illustrates an HPLC chromatogram for the purification of Dig-OBEAdCTP [IV].

FIG. IIIb illustrates the UV spectrum of Dig-OBEAdCTP [III].

FIG. IIIc illustrates the $^1$H-NMR spectrum of Dig-OBEAdCTP [III].

FIG. IVa illustrates an analytical HPLC chromatogram for Phox-OBEAdCTP [V].

FIG. IVb illustrates an HPLC chromatogram for the purification of Phox-OBEAdCTP [V].

FIG. IVc illustrates the UV spectrum of Phox-OBEAdCTP [V].

FIG. Va illustrates an analytical HPLC chromatogram for F-OBEAdCTP [VI].

FIG. Vb illustrates the UV spectrum of F-OBEAdCTP [VI].

FIG. VIa illustrates an analytical HPLC chromatogram for AE-dCTP [VIII].

FIG. VIb illustrates the UV spectrum of AE-dCTP [VIII].

FIG. VIIa illustrates an analytical HPLC chromatogram for F-AEdCTP [IX].

FIG. VIIb illustrates the UV spectrum of F-AEdCTP [IX].

FIG. VIIIa illustrates a semi-preparative HPLC chromatogram for TMRd-AEdCTP [X].

FIG. VIIIb illustrates the UV spectrum of TMRd-AEdCTP [X].

DETAILED DESCRIPTION OF THE INVENTION

The modified pyrimidine bases and nucleotides according to the invention contain a pyrimidine base with a linker arm (L) attached to the 4-position of the base. The pyrimidine bases include cytosine, uracil and thymine, and can be modified at the 5- and 6-positions by A and B moieties, respectively. A and B are independently H, an electron donating group, an electron withdrawing group, C$_1$–C$_4$ alkyl, halogen, nitro, COOH, amino, substituted amino, cyano, CONH, CSNH, COOR$_4$,

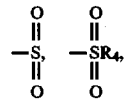

CSOR$_4$, COSR$_4$, SR$_4$, COR$_4$, CH$_2$NHR$_4$, R$_4$C=CR$_5$H or C≡C—R$_4$ where R$_4$ and R$_5$ are independently H, an electron donating group, an electron withdrawing group, C$_1$–C$_4$ alkyl, halogen, nitro, COOH, amino, substituted amino, cyano, CONH or CSNH.

A moiety X is present between the linker arm (L) and the 4-position of the pyrimidine base. X is NH, NHNH, O, S

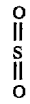

or CH$_2$.

Methods for synthesizing pyrimidine bases containing A, B and X moieties are known to those skilled in the art, and include the procedures set forth in Xu et al (J. Org. Chem., 57:3839–3845, 1992), Groziak et al (J. Org. Chem., 57:940–944, 1992), Tanaka et al (Nucleic Acids Res., Symposium Series No. 8, 533–536, 1980), Kellenbach et al (Nucleic Acids Res., 20(4):653–657, 1992), Tanaka et al (Tetrahedron Lett., 19:4755–4758, 1979), Goldman et al (Nucleosides & Nucleotides, 2(2): 175–187, 1983), Wang et al (Tetrahedron Lett., 30(50):7005–7008, 1989), Kawai et al (Nucleosides & Nucleotides, 13(5): 1189–1199, 1994), Froehler et al (Tetrahedron Lett., 34(6): 1003–1006, 1993 and Tetrahedron Lett., 33(37):5307–5310, 1992), Wagner et al (Science, 260:1510–1513, 1993), Marasco et al (J. Org. Chem., 57:6363–6365, 1992), Sanghvi et al (Nucleic Acids Res., 21(14):3197–3203, 1993), Sarfati et al (Tetrahedron, 43(15):3491–3497, 1987), and Chemistry of Nucleosides and Nucleotides (ed. L. B. Townsend, Plenum Press, N.Y., Vol. 1: pp 8–41, 1988), the contents all of which are hereby incorporated by reference.

The linker arm, -L-, which joins the pyrimidine base to the reporter group has the structure $-(CH_2)_n-(T)_q-(CH_2)_m Z_1$ or $-(CH_2)_n-(T)_q-(CH_2)_m-Z_2-(CH_2)_p Z_1$ where n, m and p are each independently an integer from 1 to 20 and q is 1 or 2, -T- is —O—,

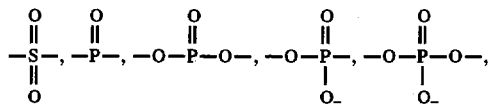

—NH— or a heterocyclic structure containing one or more Group Va or VIa elements as a ring atom, $Z_1$ is a covalent bond, —NH—, —CO—, —O—, —S— or

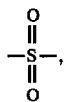

and -$Z_2$- is —NH—, —NHCO—, —NHCS—, —CONH—, —CSNH—, —O—, —S— or

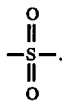

In the present invention the linker arms are based on oxygen- and sulfur-containing units which provide mixed polarity. The length of the linker arm can be adjusted according to the application. These mixed polarity spacers with a balance in hydrophillicity and hydrophobicity are more compatible in the aqueous environment surrounding DNA (i.e., the spine of hydration) than the straight hydrocarbons spacers used previously in, for example, U.S. Pat. No. 4,828,979. When linker arms according to the invention are used, modified nucleotides containing those linker arms are more efficiently incorporated into oligonucleotides or polynucleotides by nucleic acid enzymes, such as DNA polymerase. Preferred is a single ethylene glycol unit oxybis(ethylamine) linker arm, which provides the optimum distance from the DNA backbone of antigens such as biotin, digoxigenin and phenyloxazolone. Depending on the antigen, a longer linker arm may be able to maximize the interaction of the antigen with its specific antibody. These mixed polarity linker arms may be synthesized by methods known in the art (see, e.g., Bertozzi et at, J. Org. Chem., 56:4326–4329, 1991), or are commercially available as spacer phosphoramidites with reporters such as biotin and dinitrophenyl, and anchoring groups like chloesterol (Glen Research). U.S. Pat. No. 4,914,210, the contents of which are hereby incorporated by reference, discusses the use of a hydrophilic long spacer arm for the introduction of amine and thiol functionalities into oligonucleotides.

The reporter group, Rep, is a chemical group which has a physical or chemical characteristic which can be readily measured or detected by appropriate detector systems or procedures. Examples of reporter groups according to this invention can be found in U.S. Pat. Nos. 4,948,882 and 4,711,955, the contents of which are hereby incorporated by reference. Ready detectability can be provided by such characteristics as color change, luminescence, fluorescence, or radioactivity, or it can be provided by the ability of the reporter group to serve as a ligand recognition site. Such characteristics can be measured or detected, for example, by the use of conventional colorimetric, spectrophotometric, fluorometric or radioactivity sensing instrumentation, or by visual inspection.

The interactions which can be usefully initiated by the reporter group defined herein include appropriately specific and selective interactions productive of groups or complexes which are themselves readily detectable, for example, by colorimetric, spectrophotometric, fluorometric, or radioactive detection procedures. Such interactions can take the form of protein-ligand, enzyme-substrate, antibody-antigen, carbohydratelectin, protein-cofactor, protein-effector, nucleic acid-nucleic acid and nucleic acid-ligand interactions. Examples of such ligand-ligand interactions include fluorescein-anti fluorescein antibody, dinitrophenyl-dinitrophenyl antibody, biotin-avidin, oligonucleotide-complementary oligonucleotide, DNA-DNA, RNA-DNA and NADH-dehydrogenase. Either one of each of such ligand pairs may serve as a ligand recognition type reporter group. Preferred reporter groups of the invention include biotin, fluorescein, digoxigenin, phenyloxazolone, tetramethyl rhodamine, Texas Red and BODIPY (BODIPY fluorophore contains the 4,4-difluoro-4-bora-3a,4a-diaza-s-indacene unit).

General methods for joining the linker arm and reporter group to the pyrimidine base are known to those skilled in the art, and examples of those methods can be found in U.S. Pat. Nos. 4,711,955 and 4,948,882.

The sugar of the modified nucleotide of the invention can be ribose or deoxyribose, i.e., $R_1$ can be OH or H. In addition $R_2$ and $R_3$ are independently H, OH, monophosphate, diphosphate, triphosphate, thio analogs of mono-, di-, or triphosphate, O attached to a reactive phosphorous-containing group, or O protected by a blocking group. "Thio analogs of mono-, di- and triphosphate" are those phosphate analogs in which one or more oxygen atoms are replaced by sulfur. "Reactive phosphorous-containing group" as used in the present invention does not include monophosphate, diphosphate or triphosphate. Reactive phosphorous-containing groups and blocking groups are described in U.S. Pat. No. 4,948,882. In the preferred modified nucleotides of the invention, $R_1$ is H or OH, $R_2$ is OH and $R_3$ is triphosphate.

The modified nucleotides of the invention can be introduced into oligonucleotides or polynucleotides by chemical synthesis, as described in U.S. Pat. No. 4,948,882, or by the use of nucleic acid enzymes, as described in U.S. Pat. No. 4,711,955. The use of a DNA polymerase to incorporate the modified nucleotides of the invention into oligonucleotides or polynucleotides is preferred.

Nucleotides modified in accordance with the invention and oligonucleotides and polynucleotides into which the modified nucleotides have been incorporated may be used as probes in biomedical research, clinical diagnosis and recombinant DNA technology. Some uses include detecting and identifying nucleic acid-containing etiological agents, screening bacteria for antibiotic resistance, diagnosing genetic disorders, chromosomal karyotyping and identifying tumor cells. Methods for using nucleic acid hybridization probes are well known in the art and are described in more detail, for example, in U.S. Pat. No. 4,711,955.

DESCRIPTION OF THE PREFERRED EMBODIMENTS

Method of Synthesis

The compounds of the present invention are readily prepared utilizing methodology well known in the art from starting materials which themselves are either commercially available or readily prepared by known techniques.

Synthesis of an intermediate nucleotide of the invention [II] was achieved by the transamination reaction between 2'-deoxycytidine-5'-triphosphate [I] and 2,2'-oxy-bis-(ethylamine)-dihydrochloride according to the procedure of Shapiro et at, *Biochem. Biophys. Res. Comm.*, Vol. 40, p. 839 (1970), the contents of which are hereby incorporated by reference (Scheme I).

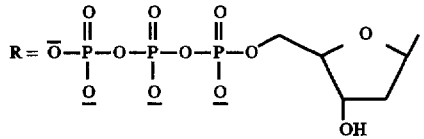

Purification of the product compound by HPLC was followed by labeling of the derivatized nucleotide [II] with a series of detectable moieties, such as biotin, digoxigenin, phenyloxazolone, fluorescein and tetramethylrhodamine, to give the preferred labeled dCTP nucleotides [III] to [VII], respectively (Schemes II, III and IV).

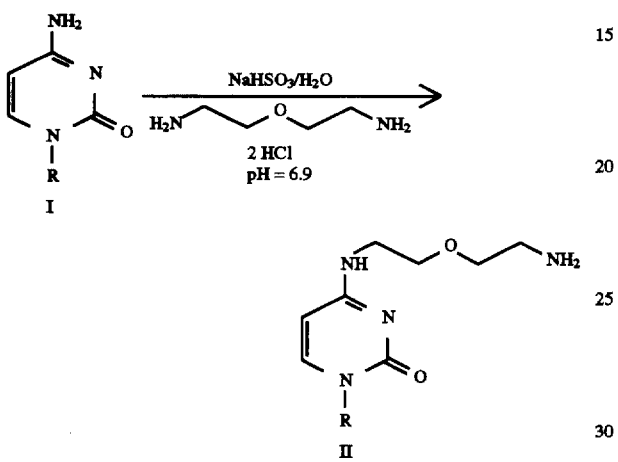

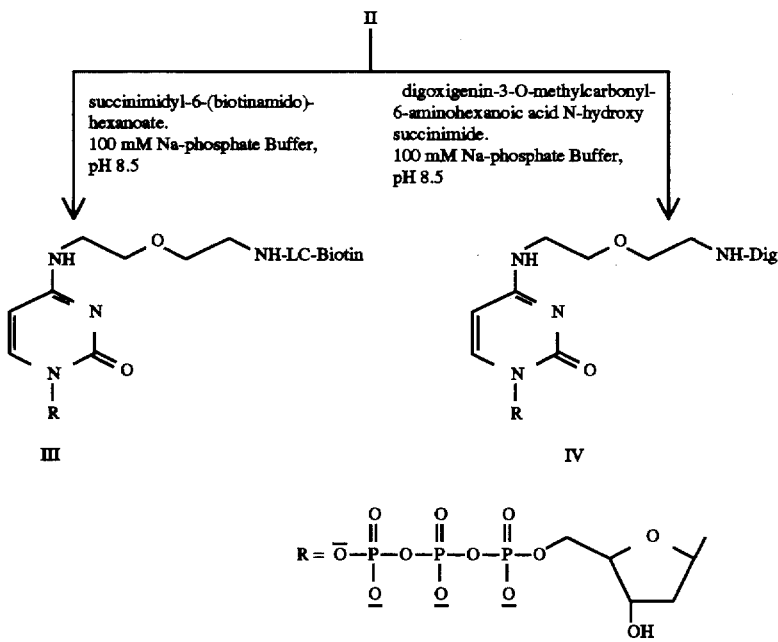

-continued
Scheme. II

Biotin-LC:

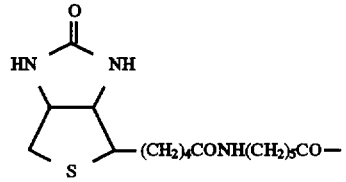
—(CH$_2$)$_4$CONH(CH$_2$)$_5$CO—

Dig:

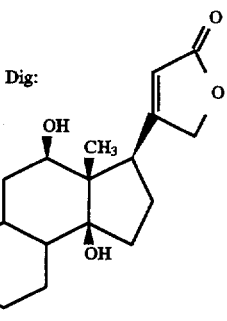
—CO(CH$_2$)$_5$NHCOCH$_2$O—

Scheme. III

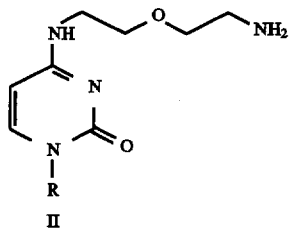
II

↓ 2-phenyl-4-ethoxymethylene-5-oxazolone.
100 mM Na-phosphate Buffer,
pH 8.5

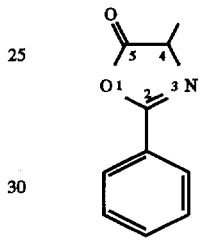
V

-continued
Scheme. III

Phox:

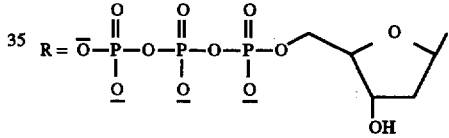

R = 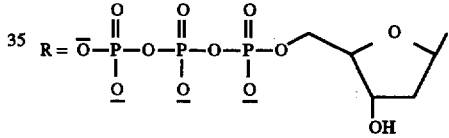

Scheme. IV

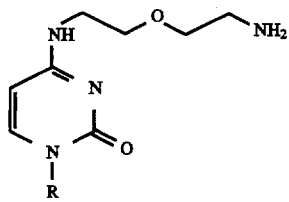
II

| 5-carboxyfluorescein-N-hydroxy-succinimide ester. 100 mM Na-phosphate Buffer, pH = 8.5 | 5-carboxytetramethylrhodamine-N-hydroxysuccinimide ester. 100 mM Na-phosphate Buffer, pH = 8.5 |

↓ ↓

-continued
Scheme. IV

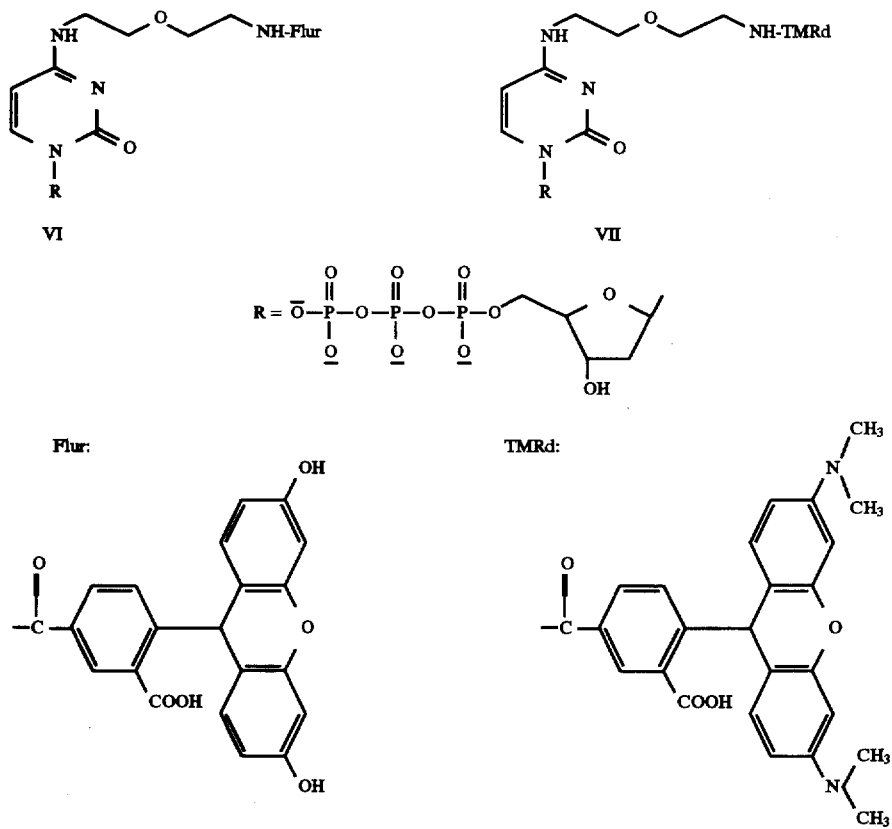

These dCTP derivatives could easily be purified by C-18 reverse-phase HPLC due to a large shift observed in their retention times as compared to their precursor [II]. The $^1$H-NMR spectra of the triethylammonium salts of [III] and [IV] were taken in D$_2$O. These revealed the characteristic proton peaks corresponding to that of H-6 and H-5 of the cytosine base, and anomeric H-1' of the sugar by comparison with the spectrum of a structurally identical nucleoside as reported in Miller et al, Bioconjugate Chem., Vol. 3, p. 74, 1992, the contents of which are hereby incorporated by reference. The ethylenic HC=C— proton of digoxigenin was clearly distinguished from the rest by comparing the spectra of [III] and [IV].

Another nucleotide intermediate [VIII] was obtained by the transamination reaction described above between 2'-deoxycytidine-5'-triphosphate [I] and ethylenediamine (Scheme V).

Scheme. V

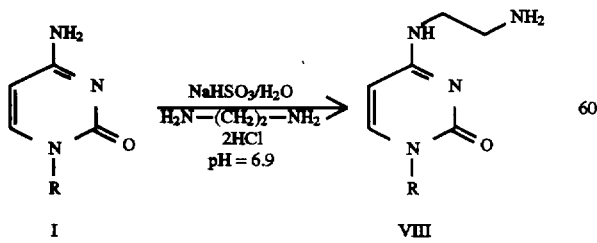

-continued
Scheme. V

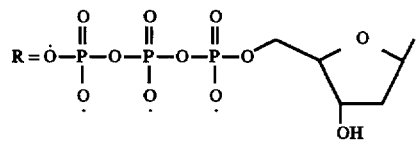

The resulting derivatized nucleotide was then labeled with a series of detectable moieties such as fluorescein and tetramethylrhodamine to give the series of labeled dCTP nucleotides [IX] and [X], respectively (Scheme VI).

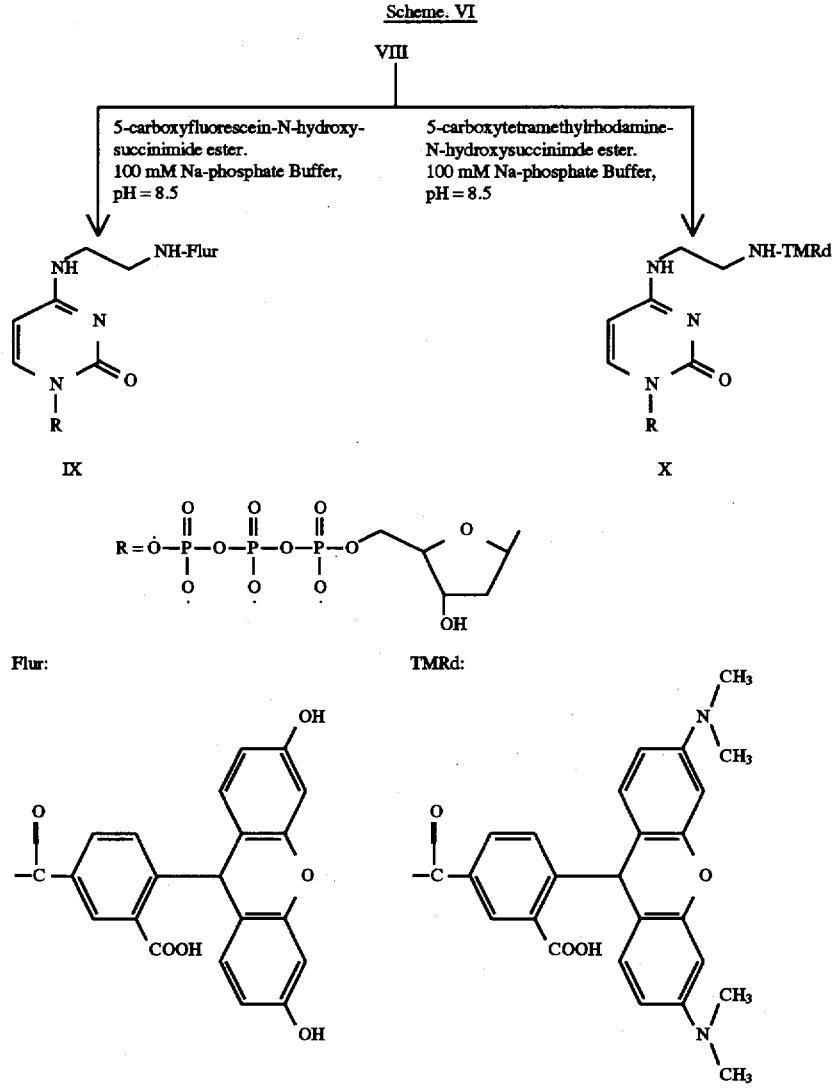

EXAMPLE I

N⁴-[2,2-oxy-bis-(ethylamine)]-2'-deoxycytidine-5'-triphosphate (OBEA-dCTP)

A solution of sodium bisulfite (2.5 g, 24 mmoles) and 2,2'-oxy-bis-(ethylamine)dihydrochloride (2.65 g, 15 mmoles) in deionized water (5 ml) was adjusted to pH 6.9 with 10M aq. NaOH followed by the addition of dCTP (100 mg, 0.2 mmoles). The resulting solution was tightly capped and incubated at 37° C. for 3 days. HPLC analysis by an analytical C-18 reverse phase column (Dynamax 300 A) using a gradient method [0% to 15% acetonitrile vs. 50 mM triethylammonium acetate (TEAA) pH=6.9 for a period of 35 min with flow rate of 1 ml/min and UV detection at 272 nm], revealed that more than 90% of the starting material ($R_t$=19.4 min) had reacted to give a later eluting compound with ($R_t$=20.5 min) which produced a positive color test upon reacting with ninhydrin (FIG. Ia). Bulk purification of the product compound was performed using a preparative column (Vydac, 22 mm×250 mm or Dynamax 300-A, 21.4 mm×250 mm) with a method similar to that discussed above. Fractions containing the product [II] (FIG. Ib) were lyophilized to give an oily residue with 40% yield. The yield was calculated assuming a molar extinction coefficient equal to that of dCTP [I] in $H_2O$ ($\epsilon_{272}$=9100).

EXAMPLE II $N_4$-[Biotinamidohexanoyl-2,2'-oxy-bis(ethylamine)]-2'-deoxycytidine-5'-triphosphate (Bio—OBEAdCTP)

A lyophilized sample of the triethylammonium salt of OBEAdCTP [II], (43 µmoles) was dissolved in 15 ml of 100 mM sodium phosphate buffer, pH 8.5 (2.5 mM). To this, a solution of succinimidyl-6-)biotinamido)hexanoate (NHS-LC-Biotin II, 30 mg, 66 µmoles) in dry N,N-dimethylformamide (0.65 ml, 100 mM) was added. After 2 hrs at room temperature and overnight at 4° C., the reaction was completed, as monitored by analytical C-18 reverse-phase HPLC using the same eluent as described for [II] except that higher acetonitrile (40%) was needed to elute the biotinylated nucleotide. The crude reaction mixture after filtration was loaded onto a preparative C-18 reverse phase column as mentioned previously (gradient of 1% to 40% acetonitrile vs. 50 mM triethylammonium acetate buffer over a period of 35 min with a flow rate of 10 ml/min). Fractions containing the biotinylated nucleotide [III] (FIG. IIa) were pooled together, and lyophilized to give 15 mg of the pure isolated product (yield 38%). This was dissolved in a minimum volume of $H_2O$, neutralized to pH 7.0. The yield was calculated on the basis of a molar extinction coefficient equal to 9100 as before. $^1$H-NMR (500 MHz, D$_2$O) δ 7.8 (S, $^1$H, H-6), 6.2 (bs, 1H, H-1'), 6.04 (s, 1H, H-5) (FIG. IIb). UV (50 mM TEAA pH 6.9) $\lambda_{max}$272 nm (FIG. IIc).

EXAMPLE III

N$^4$-[Digoxigenin-3-O-methylcarbonyl-2,2'-oxy-bis(ethylamine)]-2'-deoxycytidine-5'-triphosphate (Dig-OBEAdCTP)

To a lyophilized sample of OBEAdCTP triethylammonium salt [II], (40 μmoles) dissolved in sodium phosphate buffer (5 ml, 100 mM, pH 8.5), a solution of digoxigenin-3-O-methylcarbonyl-6-aminohexanoic acid N-hydroxy succinimide (DigNHS, 35 mg, 53 μmoles) in dry N,N-dimethylformamide (1.4 ml) was added. The reaction mixture was allowed to stand at room temperature for 2 hrs and refrigerated overnight for completion. The crude reaction mixture showed a profile in C-18 reverse-phase HPLC similar to that of the biotinylated analogue. Dig-OBEAdCTP [IV] was purified by preparative C-18 reverse phase column chromatography (FIG. IIIa) using the conditions as mentioned for [III] to give 12 mg of the pure compound (yield 28%). The yield was calculated assuming $\epsilon_{272}$=9100. $^1$H-NMR (500 MHz, D$_2$O) δ7.8 (s, 1H, H-6), 6.2 (bs, 1H, H-1'), 6.04 (s, 1H, H-5), 5.9 (s, 1H, HC=C—) (FIG. IIIb). UV (50 mM TEAA pH 6.9) $\lambda_{max}$274 nm (FIG. IIIc).

EXAMPLE IV

N$^4$-{4-[2,2'-oxy-bis(ethylamine)]-2-phenyl-5-oxazolone}-2'-deoxycytidine-5' triphosphate (Phox-OBEAdCTP)

A lyophilized sample of the triethylammonium salt of OBEAdCTP [II], (3.6 μmoles) was dissolved in 100 mM sodium phosphate buffer, pH 8.5 (4.3 mM). To this, a solution of 2-phenyl-4-ethoxymethylene-5-oxazolone (11 mg, 51 μmoles) in dry N,N-dimethylformamide (0.5 ml, 100 mM) was added. After 2 hrs at room temperature and overnight at 4° C., the reaction was completed as monitored by analytical ion exchange column (Partisil 10 SAX) using a gradient method (15% acetonitrile in 100 mM potassium phosphate buffer, pH=6.8 vs 10 mM potassium phosphate, pH=6.8 over a period of 30 min with a flow rate of 1 ml/min and UV detection at 272 nm) revealed that more than 85% of the starting materials (R$_t$=10.0 min and R$_t$=39.59 min) had converted to the product compound (R$_t$=36.5 min), (FIG. IVa). It is believed that the structure of the phenyloxazolone reporter group is as shown for labeled dCTP nucleotide [V] in Scheme III, but it should be understood that the actual structure of nucleotide [V] is what is formed by the reaction of OBEAdCTP [II] with 2-phenyl-4-ethoxymethylene-5-oxazolone, as described above. Fractions containing [V] after lyophilization were further purified by an analytical C-18 reverse phase column (Dynamax-300 A) using a gradient method (0% to 25% acetonitrile vs 50 mM triethylammonium acetate buffer pH=6.9 for a period of 25 min with a flow rate of 1 ml/min). The purified fractions (R$_t$=28.92 min), (FIG. IVb) were lyophilized to give a precipitate with 60% yield. The yield was calculated on the basis of a molar extinction coefficient equal to 9100 (FIG. IVc).

EXAMPLE V

N$^4$[5-Carboxyfluorescein-2,2'-oxy-bis(ethylamine)]-2'-deoxycytidine-5'-triphosphate (F-OBEAdCTP)

A lyophilized sample of the triethylammonium salt of OBEAdCTP [II], (4.2 mM) was dissolved in 68 μl of 100 mM sodium phosphate buffer, pH 8.5. To this, a solution of 5-carboxyfluorescein-N-hydroxysuccinimide ester (5CF-NHS) in dry N,N-dimethylformamide (2 μl, 105 mM) was added and left in darkness at 4° C. for 24 hrs. The reaction was monitored by analytical C-18 reverse-phase HPLC (Dynamax 300-A) using a gradient method (0.5% to 10% of acetonitrile vs 50 mM triethylammoniumacetate buffer, pH 6.8 over 30 min with a flow rate of 1 ml/min and UV detection at 272 nm), which revealed that most of the starting material (R$_t$=6.5 min) converted to its labeled product (R$_t$=34.0 min) (FIG. Va). Fractions containing the fluoresceinated nucleotide [VI], were collected and lyophilized to give a precipitate with 20% yield. The yield was calculated on the basis of molar extinction coefficient equal to 9100 (FIG. Vb).

EXAMPLE VI

N$^4$(ethylamine)-2'-deoxycytidine-5'-triphosphate (AEdCTP)

A solution of sodium bisulfite (2.5 g, 24 mmoles) and ethylenediamine (5 ml, 0.899 g/ml, 75 mmoles) in deionized water (5 ml) was adjusted to pH 6.9 with concentrated hydrochloric acid dropwise on ice. To this mixture, dCTP (115.2 mg, 0.22 mmoles) was added and the resulting solution was tightly capped and incubated at 37° C. for 24 hrs. HPLC analysis by an analytical C-18 reverse phase column (Dynamax 300 A) using a gradient method [0% to 15% acetonitrile vs. 50 mM triethylammonium acetate (TEAA) pH=6.9 for a period of 35 min with a flow rate of 1 ml/min and UV detection at 272 nm], revealed that most of the starting material (R$_t$=11.77 min) had reacted to give an early eluting compound (R$_t$=8.46 min) which produced a positive color test upon reacting with ninhydrin (FIG. VIa). Bulk purification of the product compound with a method similar to that described for compound [II] resulted in an oily residue with 60% overall yield. The yield was calculated assuming a molar extinction coefficient equal to that of dCTP [I] in H$_2$O ($\epsilon_{272}$=9100), (FIG. VIb).

EXAMPLE VII

N$^4$[5-Carboxyfluorescein-(ethylamine)]-2'-deoxycytidine-5'-triphosphate (F-AEdCTP)

A lyophilized sample of the triethylammonium salt of AEdCTP [VIII], was dissolved in 68 μl of 100 mM sodium phosphate buffer pH 8.5 (1.1 mM). To this, a solution of 5-carboxy-fluorescein-N-hydroxysuccinimide ester (5CF-NHS) in dry N,N-dimethylformamide (2 μl, 105 mM) was added and left in darkness at 4° C. for 24 hrs. The reaction was monitored by analytical C-18 reverse-phase HPLC column (Dynamax 300-A) using a gradient method (0.5% to 10% of acetonitrile vs 50 mM triethylammoniumacetate buffer pH 6.8, over 30 min with a flow rate of 1 ml/min and UV detection at 272 nm), which revealed that most of the starting material (R$_t$=11.77) had converted to labeled product (R$_t$=31.80 min) (FIG. VIIA). Fractions containing the fluoresceinated nucleotide [IX], were collected and lyophilized to give a precipitate with 25% yield. The yield was calculated on the basis of a molar extinction coefficient equal to 9100 (FIG. VIIb).

EXAMPLE VIII

N$^4$-[5-Carboxytetramethylrhodamine-(ethylamine)]-2'-deoxycytidine-5'-triphosphate (TMRd-AEdCTP)

To a lyophilized sample of the triethylammonium salt of AEdCTP [VIII] dissolved in 9.4 ml of 100 mM sodium phosphate buffer pH 8.5 (1.2 mM), a solution of 5-carboxytetramethyl-rhodamine-N-hydroxysuccinimide ester (5CTMRd-NHS) in dry N,N-dimethylformamide (300 µl, 44 mM) was added and placed in darkness at 4° C. for 24 hrs. The reaction was monitored by a semi-preparative C-18 reverse-phase HPLC column (Dynamax 300-A) using a gradient method (1% to 30% of acetonitrile vs 50 mM triethylammoniumacetate buffer pH 6.8, over 35 min with a flow rate of 3 ml/min and UV detection at 272 nm), which revealed that most of the starting material had converted to labeled product (R,34.0 min) (FIG. VIIIa). Fractions containing the product compound [X], were collected and lyophilized to give a precipitate with 22% yield. The yield was calculated on the basis of a molar extinction coefficient equal to 9100 (FIG. VIIIb).

We claim:

1. A compound having the structure:

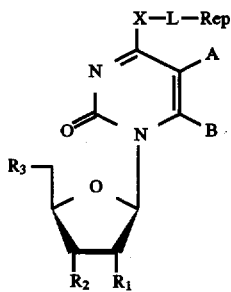

wherein:

-$R_1$ is —H or —OH;

-$R_2$ and -$R_3$ are independently —H, —OH, monophosphate, diphosphate, triphosphate, thio analogs of mono-, di-, or triphosphates, —O— attached to a reactive phosphorous-containing group or —O— protected by a blocking group;

-A and -B are independently —H, an electron donating group, an electron withdrawing group, $C_1$-$C_4$ alkyl, halogen; nitro, —COOH, amino, substituted amino, cyano, —CONH, —CSNH, —COOR$_4$

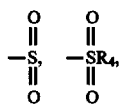

—CSOR$_4$, —COSR$_4$, —SR$_4$, —COR$_4$, —CH$_2$NHR$_4$, -R$_4$C=CR$_5$H or —C≡C—R$_4$ where R$_4$ and R$_5$ are independently H, an electron donating group, an electron withdrawing group, $C_1$-$C_4$ alkyl, halogen, nitro, COOH, amino, substituted amino; cyano, CONH or CSNH;

-X- is —NH—, —NHNH—, —O—, —S—,

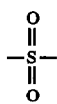

or —CH$_2$—;

Rep is a detectable reporter group; and

-L- is —(CH$_2$)$_n$-(T)$_q$—(CH$_2$)$_m$Z$_1$ or —(CH$_2$)$_n$-(T)$_q$—(CH$_2$)$_m$-Z$_2$—(CH$_2$)$_p$Z$_1$ where n, m and p are each independently an integer from 1 to 20 and q is 1 or 2, -T- is —O—, —S—,

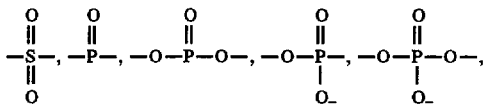

—NH— or a heterocyclic structure containing one or more Group Va or VIa elements as a ring atom, Z$_1$ is a covalent bond, —NH—, —CO—, —O—, —S— or

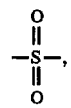

and -Z$_2$- is —NH—, —NHCO—, —NHCS—, —CONH—, —CSNH—, —O—, —S— or

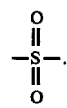

2. An oligodeoxyribonucleotide or polydeoxyribonucleotide sequence which comprises at least one compound in accordance with claim 1.

3. An oligoribonucleotide or polyribonucleotide sequence which comprises at least one compound in accordance with claim 1.

4. A compound according to claim 1, wherein -$R_1$ is —OH.

5. A compound according to claim 1, wherein -$R_1$ is —H.

6. A compound according to claim 1, wherein -A and -B are —H and -X- is —NH—.

7. A compound according to claim 1, wherein -$R_1$ is —H, —$R_2$ is —OH and $R_3$ is triphosphate.

8. A compound according to claim 1, wherein -$R_1$ is —OH, -$R_2$ is —OH and $R_3$ is triphosphate.

9. A compound according to claim 1, wherein Rep is biotin.

10. A compound according to claim 1, wherein Rep is fluorescein.

11. A compound according to claim 1, wherein Rep is digoxigenin.

12. A compound according to claim 1, wherein Rep is tetramethyl rhodamine.

13. A compound according to claim 1, wherein Rep is phenyloxazolone.

14. A compound according to claim 1 which is N$^4$-[biotinamidohexanoyl-2,2'-oxy-bis(ethylamine)]-2'-deoxycytidine-5'-triphosphate.

15. A compound according to claim 1 which is N$^4$-[digoxigenin-3-O-methylcarbonyl[2,2'-oxy-bis(ethylamine)]-2'-deoxycytidine-5'-triphosphate.

16. A compound according to claim 1 which is N$^4$-{4-[2-phenyl-5-oxazolone-2,2'-oxy-bis(ethylamine)]}-2'-deoxycytidine-5'-triphosphate.

17. A compound according to claim 1 which is N$^4$-[5-carboxyfluorescein-2,2'-oxy-bis(ethylamine)]-2'-deoxycytidine-5'-triphosphate.

18. A compound according to claim 1 which is N$^4$-[5-carboxytetramethylrhodamine-2,2'-oxy-bis(ethylamine)]-2'-deoxycytidine-5'-triphosphate.

19. A compound according to claim 1 which is N$^4$-[Texas Red-2,2'-oxy-bis(ethylamine)]-2'-deoxycytidine-5'-triphosphate.

20. A compound according to claim 1 which is N$^4$-[4-{4,4-difluoro-5-(2-thienyl)-4-bora-3a,4a-diaza-s-indacene-3- yl)-phenoxy)-acetylamino)-hexanoyl-2,2'-oxybis(ethylamino)]-2'-deoxycytidine-5'-triphosphate.

21. A compound having the structure:

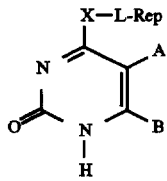

wherein:

-A and -B are independently —H, an electron donating group, an electron withdrawing group, $C_1$–$C_4$ alkyl, halogen, nitro, —COOH, amino, substituted amino, cyano, —CONH, —CSNH, —COOR$_4$,

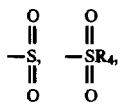

—CSOR$_4$, —COSR$_4$, —SR$_4$, —COR$_4$, —CH$_2$NHR$_4$, -R$_4$C=CR$_5$H or —C≡C—R$_4$ where R$_4$ and R$_5$ are independently H, an electron donating group, an electron withdrawing group, $C_1$–$C_4$ alkyl, halogen, nitro, COOH, amino, substituted amino, cyano, CONH or CSNH;

-X- is —NH—, —NHNH—, —O—, —S—,

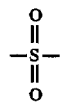

or —CH$_2$—;

Rep is a detectable reporter group; and

-L- is —(CH$_2$)$_n$-(T)$_q$—(CH$_2$)$_m$-Z$_1$ or —(CH$_2$)$_n$-(T)$_q$—(CH$_2$)$_m$-Z$_2$—(CH$_2$)$_p$Z$_1$ where n, m and p are each independently an integer from 1 to 20 and q is 1 or 2, -T- is —O—, —S—,

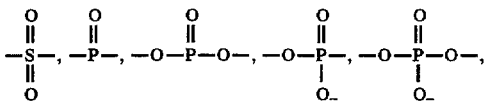

—NH— or a heterocyclic structure containing one or more Group Va or VIa elements as a ting atom, Z$_1$ is a covalent bond, —NH—, —CO—, —O—, —S— or

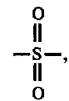

and -Z$_2$- is —NH—, —NHCO—, —NHCS—, —CONH—, —CSNH—, —O—, —S— or

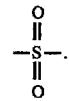

* * * * *